United States Patent [19]

Sturm et al.

[11] Patent Number: 5,069,819

[45] Date of Patent: Dec. 3, 1991

[54] THIOESTERS AND ANTIOXIDANT COMPOSITIONS CONTAINING THE SAME

[75] Inventors: Budd H. Sturm, Hartville; Joseph A. Kuczkowski, Munroe Falls, both of Ohio

[73] Assignee: The Goodyear Tire & Rubber Company, Akron, Ohio

[21] Appl. No.: 579,903

[22] Filed: Sep. 10, 1990

[51] Int. Cl.$^5$ ............... C09K 15/26; C07C 323/53
[52] U.S. Cl. ............... 252/402; 252/404; 252/405; 252/406; 560/10; 560/15; 560/152
[58] Field of Search ............... 560/10, 15, 152; 252/401, 402, 405, 404, 406

[56] References Cited

U.S. PATENT DOCUMENTS 4,772,651  9/1988  Dunski ............... 524/289

FOREIGN PATENT DOCUMENTS 60-28958  2/1985  Japan .

Primary Examiner—Jose G. Dees
Assistant Examiner—Vera C. Clarke
Attorney, Agent, or Firm—Bruce J. Hendricks

[57] ABSTRACT

The present invention relates to thioesters having the structural formula:

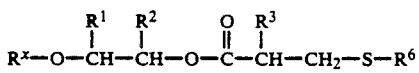

wherein $R^x$ is selected from the group of formulae consisting of:

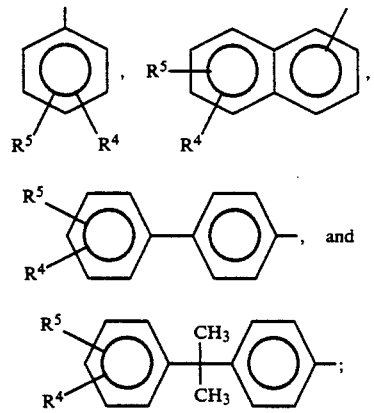

$R^1$, $R^2$ and $R^3$ are independently selected from the group of radicals consisting of hydrogen or methyl; $R^4$ and $R^5$ are independently selected from the group of radicals consisting of hydrogen, alkyls having 1 to 18 carbon atoms, aryls having 6 to 10 carbon atoms, aralkyls having 7 to 9 carbon atoms, and radicals of the formula:

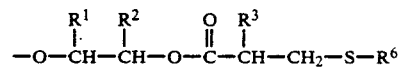

and $R^6$ is selected from the group of radials consisting of alkyls having 1 to 24 carbon atoms, aryls having 6 to 12 carbon atoms and aralkyls having 7 to 12 carbon atoms.

These thioesters are particularly useful as a synergist for conventional phenolic and amine antioxidants.

8 Claims, No Drawings

THIOESTERS AND ANTIOXIDANT COMPOSITIONS CONTAINING THE SAME

BACKGROUND OF THE INVENTION

The present invention relates to thioesters which are particularly useful as synergists when used with conventional phenolic and amine antioxidants.

In addition, the present invention relates to a two component stabilizer system for polymers.

Ester materials have been used as synergists in combination with free amine antioxidants and phenolic antioxidants. For example, U.S. Pat. No. 4,216,116 discloses a stabilization system for organic materials comprising a phenolic antioxidant and a polyethyleneoxy diester of a thiopropionic acid. Also, see U.S. Pat. Nos. 4,125,515, 4,241,217 and 4,301,296 which teach the combination of conventional free amine antioxidants with esters which function as synergists, for example, 3,6,9-trioxyaundecane-1,11-bis (3-n-dodecylthio-propionate). Whereas, the esters described in these patents have become commercially available products sold under the trademark Wingstay® SN-1 by The Goodyear Tire & Rubber Company of Akron, Ohio, those skilled in the art are constantly searching for new, improved antidegradant systems to further prolong the life of polymer products. Therefore, there exists a need for compositions which are useful in further prolonging the life of polymers and in particular, rubber compositions.

SUMMARY OF THE INVENTION

The present invention relates to a compound comprising a thioester having the following structural formula:

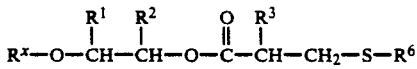

wherein $R^x$ is selected from the group of formulae consisting of:

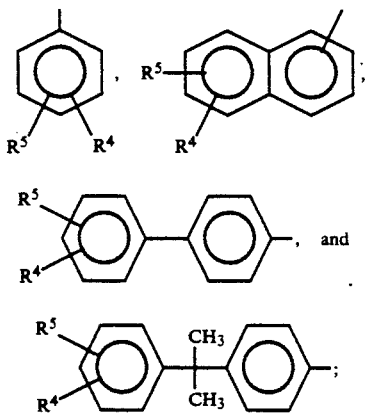

$R^1$, $R^2$ and $R^3$ are independently selected from the group of radicals consisting of hydrogen or methyl: $R^4$ and $R^5$ are independently selected from the group of radicals consisting of hydrogen, alkyls having 1 to 18 carbon atoms, aryls having 6 to 10 carbon atoms, aralkyls having 7 to 9 carbon atoms, and radicals of the formula:

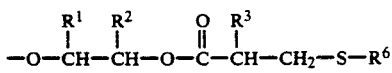

and $R^6$ is selected from the group of radicals consisting of alkyls having 1 to 24 carbon atoms, aryls having 6 to 12 carbon atoms and aralkyls having 7 to 12 carbon atoms. In addition, the present invention relates to a synergistic antioxidant system comprising the above thioester and (a) an amine antioxidant and/or a phenolic antioxidant.

DETAILED DESCRIPTION OF THE INVENTION

As discussed above, the thioesters are useful in combination with conventional phenolic and amine antioxidants. Representative examples of the above thioesters include, but are not limited to the following 3-(n-octadecylthio)propanoic acid, 2,2'-[1,4-phenylene bis (oxy)] bis ethyl diester 3-(n-dodecylthio)-propanoic acid, 2,2'-[1,4-phenylene bis (oxy)] bis ethyl diester 3-(n-octylthio)-propanoic acid, 2,2'-[1,4-phenylene bis (oxy)] bis ethyl diester 3-(n-butylthio)-propanoic acid, 2,2'-[1,4-phenylene bis (oxy)] bis ethyl diester 3-(n-dodecylthio)-propanoic acid, 2,2'-[1,4-phenylene bis (oxy)] bis propyl diester 3-(n-dodecylthio)-2-methyl-propanoic acid, 2,2'-[1,4-phenylene bis (oxy)] bis propyl diester 3-(n-dodecylthio)-2-methyl-propanoic acid, 2,2'-[1,4-phenylene bis (oxy)] bis ethyl diester 3-(n-dodecylthio)-propanoic acid, 2,2'-[1,2-phenylene bis (oxy)] bis ethyl diester 3-(n-dodecylthio)-propanoic acid, 2,2'-[1,2-phenylene bis (oxy)] bis propyl diester 3-(n-dodecylthio)-propanoic acid, 2,2'-[1,2-phenylene bis (oxy)] ethyl, propyl diester mixture 3-(n-dodecylthio)-propanoic acid, 2,2'-[1,3-phenylene bis (oxy)] bis ethyl diester 3-(n-dodecylthio)-propanoic acid, 2,2'-[1,3-phenylene bis (oxy)] bis propyl diester 3-(n-dodecylthio)-propanoic acid, 2-(2,4-dimethyl phenoxy) ethyl ester 3-(n-dodecylthio)-propanoic acid, 2-(4-isopropyl phenoxy) ethyl ester 3-(n-dodecylthio)-propanoic acid, 2-(4-sec-butyl phenoxy) propyl ester 3-(n-dodecylthio)-propanoic acid, 2-(4-nonyl phenoxy) ethyl ester 3-(n-dodecylthio)-propanoic acid, 2-(4-nonyl phenoxy) propyl ester 3-(n-dodecylthio)-propanoic acid, 2-(2,4-dinonyl phenoxy) ethyl ester 3-(n-dodecylthio)-propanoic acid, 2-(2,4-dinonyl phenoxy) propyl ester 3-(n-dodecylthio)-propanoic acid, 2-(4-isopropyl phenoxy) propyl ester 3-(n-dodecylthio)-propanoic acid, 2,2'-[4,4'-(dimethylmethylene bis) phenoxy] bis ethyl ester 3-(n-dodecylthio)-propanoic acid, 2,2'-[4,4'-(dimethylmethylene bis) phenoxy] bis propyl diester 3-(n-dodecylthio)-propanoic acid, 2,2'-[4,4'-(dimethylmethylene bis) phenoxy] ethyl, propyl diester mixture 3-(n-dodecylthio)-propanoic acid, 2,2'-[1,1'-biphenyl-4,4'-bis (oxy)] bis propyl diester 3-(n-dodecylthio)-propanoic acid, 2,2'-[naphthylene-1,5-bis (oxy)] bis propyl diester 3-(n-dodecylthio)-propanoic acid, 2,2'[naphthylene-1,5-bis (oxy)] ethyl, propyl diester mixture 3-(n-dodecylthio)-propanoic acid, 2,2'-[2,5-di-tert-butyl-1,4-phenylene bis (oxy)] bis ethyl diester 3-(n-dodecylthio)-propanoic acid, 2,2'-[2,5-di-tert-butyl-1,4-phenylene bis (oxy)] bis propyl diester.

With respect to the above structural formula for the thioester, preferably $R^1$ is methyl when $R^2$ is hydrogen, $R^2$ is methyl when $R^1$ is hydrogen, $R^3$ is hydrogen, $R^4$ is a radical of the formula:

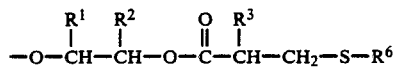

$R^5$ is hydrogen and $R^6$ is an alkyl having 6 to 14 carbon atoms.

The thioesters of the present invention may be prepared from a starting material such as a phenolic compound including but not limited to hydroquinone, resorcinol, pyrocatechol, and monoalkyl or dialkyl phenols. Representative of the monoalkyl and dialkyl phenols are para cresol, 2,4-dimethyl phenol, para isopropyl phenol, para butyl phenol, para tertiary butyl phenol, para nonyl phenol, and dinonyl phenol. The phenolic material is reacted with ethylene or propylene carbonate to form an ether alkyl alcohol intermediate. The reaction is conducted at a temperature ranging from about 120° C. to about 215° C. Preferably, the reaction temperature ranges from about 140° C. to about 180° C.

The reaction between the phenolic compound and the carbonate is generally conducted in the presence of a catalyst. Representative examples of catalysts which may be used in the present invention include dibutyltin oxide, tetraalkylammonium bromide, lithium hydroxide, potassium hydroxide, sodium hydroxide and the like. Preferably, the catalyst is lithium hydroxide or potassium hydroxide. The amount of catalyst which may be used to form the ether alkyl alcohol intermediate will depend upon the amount of reactants and temperature of the reaction. Generally speaking, the amount of catalyst ranges from about 0.001 grams to about 2.0 grams per mole of phenol. Preferably, from about 0.1 grams to 1.0 grams per mole of phenol is used.

The mole ratio of carbonate to active phenol ranges from about 1:1 to 2:1. Preferably, the mole ratio of carbonate to active phenol ranges from about 1.1:1.

In a separate reaction, an alkylthiopropionate ester is prepared by reacting a thiol with a lower alkyl ester of acrylic or methacrylic acid such as ethyl acrylate or methyl methacrylate. Representative of suitable thiols include methanethiol, ethanethiol, propanethiol, butanethiol, pentanethiol, hexanethiol, heptanethiol, octanethiol, nonanethiol, decanethiol, undecanethiol, dodecanethiol, tridecanethiol, tetradecanethiol, pentadecanethiol, hexadecanethiol, heptadecanethiol, octadecanethiol, nonadecanethiol, eicosanethiol, heneicosanethiol, docosanethiol, tricosanethiol, and tetracosanethiol. Preferably, dodecanethiol is used. The molar ratio of the thiol to the lower alkyl ester of acrylic or methacrylic acid may range from about 1:1 to about 1:2 with a range of from about 1:1.1 to 1:1.5 being preferred. The reaction may be conducted at a temperature ranging from about 0° C. to about 200° C. with a temperature of from about 25° C. to about 65° C. being preferred. Suitable catalysts for this reaction include lithium hydroxide, potassium hydroxide, sodium hydroxide and benzyl trimethyl ammonium hydroxide. Preferably, benzyl trimethyl ammonium hydroxide is used.

The ether alkyl alcohol intermediate and the alkylthiol propionate ester are reacted to form the compositions of the present invention. The reaction is carried out under vacuum at a temperature ranging from about 100° C. to about 185° C. Suitable catalysts for the reaction include dibutyltin oxide, lithium hydroxide, potassium hydroxide, sodium hydroxide and the like. The amount of catalyst may range from about 0.01 grams to 2.0 grams per mole of ether alkyl alcohol intermediate. Preferably, from about 0.25 grams to 1.0 grams per mole of ether alkyl alcohol intermediate is used.

The mole ratio between the ether alkyl alcohol intermediate and the alkylthiopropionate ester will vary depending on the desired product. Generally speaking, the mole ratio will range from about 1:1 to 1:2.5. Preferably, the mole ratio will range from about 1:1.1 to 1:2.2.

Conventional amine antioxidants may be used in combination with the ester of the present invention. Representative of the amine antioxidants which may be used include N,N'-di-substituted-p-phenylene diamines, substituted diphenylamines, and both polymerized and non-polymerized derivatives of 2,2,4-trimethyl-1,2-dihydroquinoline as well as the amide and imide age resistors. The derivatives of 2,2,4-trimethyl-1,2-dihydroquinoline are disclosed in U.S. Pat. No. 3,244,683 which is incorporated herein by reference in its entirety. Representative amide and imide age resisters are described in U.S. Pat. No. 3,658,769 which is incorporated herein in its entirety. Representative of the N,N'-di-substituted-p-phenylene diamines have the following structural formula:

wherein $R^7$ and $R^8$ are independently selected from the group of radicals consisting of alkyls having 3 to 12 carbon atoms, aryls having 6 to 12 carbon atoms, and aralkyls having 7 to 12 carbon atoms. Representative of the diphenylamines which may be used in the present invention are of the formula:

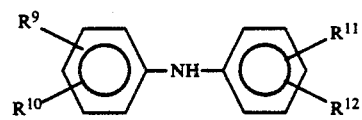

wherein $R^9$, $R^{10}$, $R^{11}$ and $R^{12}$ are independently selected from the group of radicals consisting of hydrogen, alkyls having 1 to 20 carbon atoms and aralkyls having 7 to 12 carbon atoms. Amides which may be used in the present invention are of the structure:

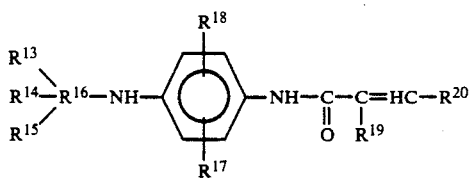

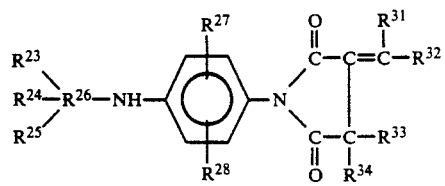

wherein $R^{16}$ is selected from the group of radicals consisting of arylenes having 6 to 12 carbon atoms, $R^{13}$ and $R^{14}$ are independently selected from the group of radicals consisting of hydrogen, alkyls having from 1 to 4 carbon atoms and alkoxys having from 1 to 4 carbon atoms, $R^{15}$ is selected from the group of radicals consisting of hydrogen, alkyls having from 1 to 4 carbon atoms, alkoxys having from 1 to 4 carbon atoms and a radical having the following structural formula:

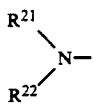

wherein $R^{21}$ is selected from the group of radicals consisting of alkyls having from 1 to 12 carbon atoms, cycloalkyls having from 5 to 12 carbon atoms, aryls having from 6 to 12 carbon atoms and aralkyls having from 7 to 13 carbon atoms and $R^{22}$ is selected from the group of radicals consisting of hydrogen and alkyls having from 1 to 12 carbon atoms and wherein $R^{17}$ and $R^{18}$ are selected from the group of radicals consisting of hydrogen, alkyls having from 1 to 4 carbon atoms, $R^{19}$ is selected from the group of radicals consisting of hydrogen, alkyls having from 1 to 4 carbon atoms, aryls having from 6 to 12 carbon atoms, aralkyls having from 7 to 13 carbon atoms, cycloalkyls having from 5 to 12 carbon atoms, carboxymethyl radicals and carbalkoxymethyl radicals, and $R^{20}$ is selected from the group of radicals consisting of hydrogen, alkyls having from 1 to 4 carbon atoms, aryls having from 6 to 12 carbon atoms, cycloalkyls having from 5 to 12 carbon atoms, carboxyl radicals and carbalkoxy radicals. Preferably $R^{13}$, $R^{14}$ and $R^{15}$ are each hydrogen. $R^{16}$ is preferably an arylene having 6 carbon atoms. $R^{17}$ and $R^{18}$ are preferably hydrogen. Preferably, $R^{19}$ is an alkyl having 1 carbon atom, $R^{20}$ is hydrogen, and $R^{21}$ is an alkyl having 1 carbon atom.

Imides which may be used in combination with the ester of the present invention may have the following structural formula:

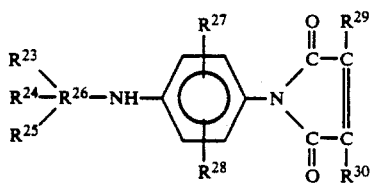

and wherein $R^{26}$ is selected from the group of radicals consisting of arylenes having 6 to 12 carbon atoms, $R^{23}$ and $R^{24}$ are independently selected from the group of radicals consisting of hydrogen, alkyls having from 1 to 4 carbon atoms and alkoxys having from 1 to 4 carbon atoms, $R^{25}$ is selected from the group of radicals consisting of hydrogen, alkyls having from 1 to 4 carbon atoms, alkoxys having from 1 to 4 carbon atoms and a radical having the following structural formula:

wherein $R^{35}$ is selected from the group of radicals consisting of alkyls having from 1 to 12 carbon atoms, cycloalkyls having from 5 to 12 carbon atoms, aryls having from 6 to 12 carbon atoms and aralkyls having from 7 to 13 carbon atoms and $R^{36}$ is selected from the group of radicals consisting of hydrogen and alkyls having from 1 to 12 carbon atoms and wherein $R^{27}$ and $R^{28}$ are alkyls having from 1 to 4 carbon atoms, and wherein $R^{29}$, $R^{30}$, $R^{31}$, $R^{32}$, $R^{33}$ and $R^{34}$ are independently selected from the group of radicals consisting of hydrogen and alkyls having 1 to 4 carbon atoms. Preferably, $R^{23}$ and $R^{24}$ are hydrogen, $R^{25}$ is hydrogen, $R^{26}$ is an arylene having 6 carbon atoms, $R^{27}$ is hydrogen, $R^{28}$ is hydrogen, $R^{29}$ is hydrogen, $R^{30}$ is hydrogen, $R^{31}$ is hydrogen, $R^{32}$ is hydrogen, $R^{33}$ is hydrogen, and $R^{34}$ is hydrogen.

Specific amines which may be used in combination with the esters of the present invention include
N,N'-diphenyl-p-phenylenediamine,
N,N'-di-beta-naphthyl-p-phenylenediamine,
N-o-tolyl-N'-phenyl-p-phenylenediamine,
N,N-di-p-tolyl-p-phenylenediamine,
N-1,3-dimethylbutyl-N'-phenyl-p-phenylenediamine,
N-1,4-dimethylpetyl-N'-phenyl-p-phenylenediamine,
N-isopropyl-N'-phenyl-p-phenylenediamine,
N-1-methylpropyl-N'-phenyl-p-phenylenediamine,
N-cyclohexyl-N'-phenyl-p-phenylenediamine,
N,N'-bis-(1-ethyl-3-methylpentyl)-p-phenylenediamine,
N,N'-bis-(1,4-dimethylpentyl)-p-phenylenediamine,
N,N'-bis-(1-methylpropyl)-p-phenylenediamine,
4,4'-bis-(di-alpha-methylbenzyl)-diphenylamine.
4,4'-dioctyldiphenylamine, 4,4'-dinonyldiphenylamine,
polymerized-2,2,4-trimethyl-1,2-dihydroquinoline,
6-dodecyl-1,2-dihydro-2,2,4-trimethylquinoline,
6-ethoxy-1,2-dihydro-2,2,4-trimethylquinoline,
N-(4-anilinophenyl)methacryamide,
N-(4-anilinophenyl)maleimide,
N-(4-anilinophenyl)itaconimide,
N-(4-anilinophenyl)citraconimide,
N-[4-(4-methylanilino)phenyl]maleimide,
N-[4-(4-methylanilino)phenyl]itaconimide,
N-[4-(4-methoxyanilino)phenyl]maleimide,
N-[4-(4-methoxyanilino)phenyl]itaconimide, N-[4-(4-ethoxyanilino)phenyl]maleimide,
N-[4-(4-ethoxyanilino)phenyl]itaconimide,
N-[4-(4-ethoxyanilino)phenyl]citraconimide,
N-(4-anilinophenyl)phenylmaleimide,
N-[4-(4-N,N-dimethylaminoanilino)phenyl]maleimide,
N-(4-anilinophenyl)acrylamide,
N-(4-anilinophenyl)methacrylamide,
N-(4-anilinophenyl)cinnamamide,
N-(4-anilinophenyl)crotonamide,
N-[4-(4-methylanilino)phenyl]acrylamide,
N-[4-(4-methylanilino)phenyl]methacrylamide,
N-[4-(4-methoxyanilino)phenyl]acrylamide,
N-[4-(4-methoxyanilino)phenyl]methacrylamide,
N-[4-(4-ethoxyanilino)phenyl]acrylamide,
N-[4-(4-ethoxyanilino)phenyl]methacrylamide,
N-[4-(4-N,N-dimethylaminoanilino)phenyl]acrylamide,
N-(4-anilinophenyl)maleamic acid,
N-(4-anilinophenyl)itaconamic acid,
N-[4-(4-methylanilino)phenyl]maleamic acid, and
N-(4-anilinophenyl)citraconamic acid.

The level of amine compound is from about 0.25 to 5.0 parts by weight per 100 parts by weight of polymer. Preferably, the level of amine compound is from about 0.5 to 2.0 parts by weight.

Phenolic antioxidants also benefit by the presence of the ester of the present invention. One example of a conventional phenolic antioxidant is represented by the following structural formula:

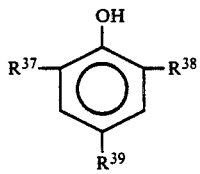

wherein $R^{37}$ and $R^{38}$ are selected from the group of radicals consisting of hydrogen, tertiary alkyls having 4 to 9 carbon atoms, cycloalkyls having 5 to 12 carbon atoms and aralkyls having 7 to 12 carbon atoms and wherein $R^{39}$ is selected from the group of radicals consisting of alkyls having 1 to 20 Carbon atoms, cycloalkyls having 5 to 12 carbon atoms and aralkyls having 7 to 12 carbon atoms.

Specific examples of phenolic antioxidants of the above structural formula include 2,6-di-tertiarybutyl-4-methyl phenol, 2-tertiaryoctyl-4,6-ditertiarybutyl phenol, 2,4,6-tris-(α-methylbenzyl)phenol, 4-nonylphenol, 2,4-dinonylphenol, and 2,4-bis(α,α-dimethylbenzyl)-6-tertiarybutylphenol. A preferred phenolic antioxidant of the above structural formula is Wingstay ®-C which is commercially available from The Goodyear Tire & Rubber Company of Akron, Ohio.

Additional phenolic antioxidants which may be used in combination with the ester of the present invention are the alkylated reaction products of simple phenols and dicyclopentadiene. Examples of such phenolic antioxidants are described in U.S. Pat. No. 3,305,522 which is incorporated herein by reference. A commercially available antioxidant of this type is sold under the trademark Wingstay ®-L from The Goodyear Tire & Rubber Company of Akron, Ohio.

Additional phenolic antioxidants which may be used in combination with the ester of the present invention are described and illustrated in U.S. Pat. No. 3,756,549 and U.S. Pat. No. 3,080,338, both of which are incorporated herein by reference.

The level of the phenolic antioxidant may vary and range from about 0.10 to 10 parts by weight per 100 parts by weight of the polymer. Preferably, the level of phenolic antioxidant ranges from about 0.25 to about 1.25 parts by weight.

The weight ratio of the ester of the present invention to either the amine or phenolic antioxidants may vary. Generally speaking, the weight ratio of amine or phenolic antioxidant to ester ranges from about 10:1 to 1 to 1:10. Preferably, the weight ratio ranges from about 5:1 to about 1:5.

Various polymers may be stabilized by use of the ester of the present invention and the amine or phenolic antioxidant. Representative polymers include homopolymers and copolymers of monoolefins, e.g., polypropylene, polyethylene and ethylene/propylene copolymers. The ester in the present invention may also be used with sulfur vulcanizable elastomers. The term "sulfur vulcanizable elastomers or rubber" as used herein embraces both natural and all its various low and reclaim forms as well as various synthetic rubbers. Representative synthetic polymers are the homopolymerization products of butadiene and its homologues and derivatives, as for example, methylbutadiene, dimethylbutadiene and pentadiene as well as copolymers such as those formed from butadiene or its homologues or derivatives with other unsaturated organic compounds. Among the latter are acetylene e.g. vinyl acetylene: olefins, for example, isobutylene, which copolymerizes with isoprene to form butyl rubber: vinyl compounds, for example vinylchloride, acrylic acid, acrylonitrile (which polymerize with butadiene to form NBR), methacrylic acid and styrene, the latter compound polymerizing with butadiene to form SBR as well as vinyl esters and various unsaturated aldehydes, ketones and ethers, e.g., acrolein, methyl isopropenyl ketone and vinylethyl ether. Also included are the various synthetic rubbers prepared by the homopolymerization of isoprene and the copolymerization of isoprene with other diolefins and various unsaturated organic compounds. Also included are the synthetic rubbers such as 1,4-cis polybutadiene and 1,4-cis polyisoprene and similar synthetic rubbers such as EPDM. The preferred rubbers for use with the hydroformylated rubber are polybutadiene, butyl rubber, EPDM, polybutadiene-styrene copolymers and polyisoprene.

The thioester of the present invention may be compounded in either productive or nonproductive stock. Incorporation of the ester into the polymer may be accomplished by conventional means of mixing such as by the use of Banburys, Brabenders, etc.

The following examples are provided to illustrate but not limit the scope of the present invention.

EXAMPLE 1

Preparation of 3-(n-dodecylthio)-propanoic acid, methyl ester

Into a 1 liter 3 necked flask equipped with a mechanical stirrer, Claissen adaptor, thermometer and dropping funnel was charged 404 grams of 98% 1-dodecanethiol with stirring to 0.7 grams of Triton B (benzyltrimethyl ammonium hydroxide) and 180.6 grams of 99% methylacrylate. The addition was over a period of ½ hour and the temperature of the reaction mixture increased form 30° C. to 56° C. The reaction was stirred an extra hour wherein the temperature dropped from 56° C. to 35° C. The reaction mixture was stripped at 92° C. and 10 mm pressure. 580 grams of product was obtained. Product analysis by GC indicated a purity of 99%.

EXAMPLE 2

Preparation of 3-(n-dodecylthio)-propanoic acid, methyl ester

Into the same type of equipment used in Example 1 was charged 405 grams of 98% 1-dodecanethiol with stirring to 1.0 grams of LiOH•H$_2$O and 181 grams of 99% methyl acrylate. The addition was over a period of 20 minutes and the temperature increased to 80°-85° C. The reaction was stirred an extra 2 hours at 85°-95° C. The reaction mixture was then stripped at 122° C. and 10 mm pressure. 582 grams of product was obtained. Product analysis by GC indicated a purity of 92.1%.

EXAMPLE 3

Preparation of 3-(n-dodecylthio)-2-methyl-propanoic acid, methyl ester

Into the same type equipment used in Example 1 202 grams of 98% 1-dodecanthiol was added to 1.0 grams of KOH and 112 grams methylmethacrylate with stirring over a 10 minute period. The reaction mixture went from 70° C. to 98° C. The reaction mixture was stirred an extra hour at 98° C. to 93° C. and slowly heated up to 122° C. over a 5 hour period. The reaction mixture was stripped at 125° C. and 20 mm pressure. GC analysis indicated a purity of 93.2% product. 300 grams filtered product was obtained.

EXAMPLE 4

Preparation of 3-(n-butylthio)-propanoic acid, methyl ester

Into the same type of equipment used in Example 1, 90 grams of 1-butylthiol was added over a ½ hour period with stirring to 0.7 grams of benzyl trimethyl ammonium hydroxide and 180.6 grams of methylacrylate. Over the 1.5 hour period, the temperature of the reaction went from 22° C. to 62° C. The reaction was stirred an extra 3 hours wherein the temperature went from 62° C. to 28° C. The reaction mixture was stripped at 104° C. and 15 mm pressure. 188 grams of product was obtained having a purity of approximately 94% as measured by GC analysis.

EXAMPLE 5

Preparation of 3-(n-octylthio)-propanoic acid, methyl ester

Into the same type of equipment used in Example 1, 146 grams of 1-octylthiol was added over a 40 minute period with stirring to 0.7 grams of benzyl trimethyl ammonium hydroxide and 180.6 grams of methylacrylate. Over the ½ hour period, the temperature of the reaction went from 25° C. to 60° C. The reaction was stirred an extra 3.0 hours wherein the temperature went from 60° C. to 28° C. The reaction mixture was stripped at 102° C. and 15 mm pressure. 333 grams of product was obtained having a purity of approximately 96.4% as measured by GC analysis.

EXAMPLE 6

Preparation of 3-(n-octadecylthio)-propanoic acid, methyl ester

Into the same type of equipment used in Example 1, 72 grams of 1-octadecylthiol was added over a ½ hour period with stirring to 0.35 grams of benzyl trimethyl ammonium hydroxide and 90.3 grams of methylacrylate. Over the ½ hour period, the temperature of the reaction went from 25° C. to 42° C. The reaction was stirred an extra 1.3 hours wherein the temperature went from 42° C. to 65° C. The reaction mixture was stripped at 156° C. and 10 mm pressure. 94 grams of product was obtained having a purity of approximately 96% as measured by GC analysis.

EXAMPLE 7

Preparation of 3-(crude sec-dodecylthio)-propanoic acid, methyl ester

Into the same type of equipment used in Example 1, 202 grams of a crude secondary C$_{12}$ mercaptan was added over a 1 hour period with stirring to 0.7 grams of benzyl trimethyl ammonium hydroxide and 180.6 grams of methylacrylate. Over the ½ hour period, the temperature of the reaction went from 18° C. to 52° C. The reaction was stirred an extra 3.0 hours wherein the temperature went from 52° C. to 30° C. The reaction mixture was stripped at 104° C. and 15 mm pressure. 305 grams of product was obtained having a purity of approximately 96% as measured by GC analysis.

EXAMPLE 8

Preparation of 3-(n-octadecylthio)propanoic acid, 2,2'-[1,4-phenylene bis (oxy)] bis ethyl diester Into a 1 liter 3 necked flask equipped with a mechanical stirrer condenser, side arm with bubbler, thermometer and Claissen adapter was added 100 grams of hydroquinone, 1.0 grams of LiOH•H$_2$O and 195 grams of 98% ethylene carbonate. The mixture was heated with stirring for 6 hours at 150°-156° C. 208 grams of product was obtained. GPC analysis in THF indicated a purity of 93.6% of 2,2'-[1,4-phenylene bis (oxy)] bis ethanol.

Into a 1 liter 3 necked flask equipped with a mechanical stirrer, Claissen adaptor attached to a distillation head, thermometer, overhead takeoff, ice bath and vacuum means was charged 77.5 grams of the ester product of Example 6, 21.0 grams of the above reaction mixture containing the ether alkyl alcohol intermediate and 0.25 grams of LiOH•H$_2$O. The reaction mixture was heated with vacuum with stirring for 2 hours at 150°-162° C.

91.5 grams of product was obtained. GPC analysis indicated 73.8% of the disubstituted product and 20.6% of the monosubstituted product.

EXAMPLE 9

Preparation of 3-(n-dodecylthio)propanoic acid, 2,2'-[1,4-phenylene bis (oxy)] bis ethyl diester Into a 1 liter 3 necked flask equipped with a mechanical stirrer condenser, side arm with bubbler, thermometer and Claissen adapter was added 100 grams of hydroquinone, 1.0 grams of LiOH•H$_2$O and 195 grams of 98% ethylene carbonate. The mixture was heated with stirring for 6 hours at 150°-156° C. 208 grams of product was obtained. GPC analysis in THF indicated a purity of 93.6% of 2,2'-[1,4-phenylene bis (oxy)] bis ethanol.

Into a 1 liter 3 necked flask equipped with a mechanical stirrer, Claissen adaptor attached to a distillation head, thermometer, overhead takeoff, ice bath and vacuum means was charged 153 grams of the ester product of Example 1, 53 grams of the above reaction mixture containing the ether alkyl alcohol intermediate and 1.0 grams of LiOH•H₂O. The reaction mixture was heated with vacuum with stirring for 1 hour at 145°-155° C.

192 grams of product was obtained. GPC analysis indicated 79.6% of the disubstituted product and 6.5% of the monosubstituted product.

EXAMPLE 10

Preparation of 3-(n-octylthio)propanoic acid 2,2'-[1,4-phenylene bis (oxy)] bis ethyl diester Into a 1 liter 3 necked flask equipped with a mechanical stirrer condenser, side arm with bubbler, thermometer and Claissen adapter was added 110 grams of hydroquinone, 2.8 grams of tetraethylammonium bromide and 202 grams of 98% ethylene carbonate. The mixture was heated with stirring for 5 hours at 148°-152° C. 209 grams of product was obtained. GPC analysis in THF indicated a purity of 87.5% of 2,2'-[1,4-phenylene bis (oxy)] bis ethanol.

Into a 1 liter 3 necked flask equipped with a mechanical stirrer, Claissen adaptor attached to a distillation head, thermometer, overhead takeoff, ice bath and vacuum means was charged 121 grams of the ester product of Example 5, 51.5 grams of the above reaction mixture containing the ether alkyl alcohol intermediate and 1.5 grams of dibutyltin oxide. The reaction mixture was heated with vacuum with stirring for 2 hours at 140°-150° C.

156 grams of product was obtained. GPC analysis indicated 26.6% of the disubstituted product and 37.3% of the monosubstituted product.

EXAMPLE 11

Preparation of 3-(n-butylthio)propanoic acid, 2,2'-[1,4-phenylene bis (oxy)] bis ethyl diester Into a 1 liter 3 necked flask equipped with a mechanical stirrer condenser, side arm with bubbler, thermometer and Claissen adapter was added 110 grams of hydroquinone, 2.8 grams of tetraethylammonium bromide and 202 grams of 98% ethylene carbonate. The mixture was heated with stirring for 5 hours at 148°-152° C. 209 grams of product was obtained. GPC analysis in THF indicated a purity of 87.5% of 2,2'-[1,4-phenylene bis (oxy)] bis ethanol.

Into a 1 liter 3 necked flask equipped with a mechanical stirrer, Claissen adaptor attached to a distillation head, thermometer, overhead takeoff, ice bath and vacuum means was charged 92 grams of the ester product of Example 4, 51.5 grams of the above reaction mixture containing the ether alkyl alcohol intermediate and 1.5 grams of dibutyltin oxide. The reaction mixture was heated with vacuum with stirring for 2 hours at 142°-152° C.

127 grams of product was obtained. GPC analysis indicated 47.0% of the disubstituted product and 21.4% of the monosubstituted product.

EXAMPLE 12

Preparation of 3-(n-dodecylthio)propanoic acid, 2,2'-[1,4-phenylene bis (oxy)] bis propyl diester Into a 1 liter 3 necked flask equipped with a mechanical stirrer condenser, side arm with bubbler, thermometer and Claissen adapter was added 110 grams of hydroquinone, 1.0 grams of LiOH•H₂O and 230 grams of 98% propylene carbonate. The mixture was heated with stirring for 10 hours at 163°-168° C. 234 grams of product was obtained. GPC analysis in THF indicated a purity of 91.3% of 2,2'-[1,4-phenylene bis (oxy)] bis propanol.

Into a 1 liter 3 necked flask equipped with a mechanical stirrer, Claissen adaptor attached to a distillation head, thermometer, overhead takeoff, ice bath and vacuum means was charged 157 grams of the ester product of Example 1, 61.25 grams of the above reaction mixture containing the ether alkyl alcohol intermediate and 0.5 grams of KOH. The reaction mixture was heated with vacuum with stirring for 1 hour at 160°-168° C.

198.5 grams of product was obtained. GPC analysis indicated 62.5% of the disubstituted product and 28.0% of the monosubstituted product.

EXAMPLE 13

Preparation of 3-(n-dodecylthio)-2-methyl-propanoic acid, 2,2'-[1,4-phenylene bis (oxy)] bis propyl diester Into a 1 liter 3 necked flask equipped with a mechanical stirrer condenser, side arm with bubbler, thermometer and Claissen adapter was added 110 grams of hydroquinone, 1.0 grams of KOH and 230 grams of 98% propylene carbonate. The mixture was heated with stirring for 8 hours at 163°-168° C. 234 grams of product was obtained. GPC analysis in THF indicated a purity of 96.8% of 2,2'-[1,4-phenylene bis (oxy)] bis propanol.

Into a 1 liter 3 necked flask equipped with a mechanical stirrer, Claissen adaptor attached to a distillation head, thermometer, overhead takeoff, ice bath and vacuum means was charged 167 grams of the ester product of Example 3, 61.25 grams of the above reaction mixture containing the ether alkyl alcohol intermediate and 0.75 grams of KOH. The reaction mixture was heated with vacuum with stirring for 1 hour at 155°-162° C.

210 grams of product was obtained. GPC analysis indicated 32.3% of the disubstituted product and 62.3% of the monosubstituted product.

EXAMPLE 14

Preparation of 3-(n-dodecylthio)-2-methyl-propanoic acid, 2,2'-[1,4-phenylene bis (oxy)] bis ethyl diester Into a 1 liter 3 necked flask equipped with a mechanical stirrer condenser, side arm with bubbler, thermometer and Claissen adapter was added 110 grams of hydroquinone, 1.0 grams of LiOH•H₂O and 195 grams of 98% ethylene carbonate. The mixture was heated with stirring for 6 hours at 150°-156° C. 208 grams of product was obtained. GPC analysis in THF indicated a purity of 93.6% of 2,2'-[1,4-phenylene bis (oxy)] bis ethanol.

Into a 1 liter 3 necked flask equipped with a mechanical stirrer, Claissen adaptor attached to a distillation head, thermometer, overhead takeoff, ice bath and vacuum means was charged 180 grams of the ester product of Example 3, 53.0 grams of the above reaction mixture containing the ether alkyl alcohol intermediate and 1.0 grams of LiOH•H₂O. The reaction mixture was heated with vacuum with stirring for 2 hours at 155°-158° C.

The desired product was obtained. GPC analysis indicated 72.4% of the disubstituted product and 19.2% of the monosubstituted product.

EXAMPLE 15

Preparation of 3-(n-dodecylthio)-2-methyl-propanoic acid, 2,2'-[1,4-phenylene bis (oxy)]bis propyl diester Into a 1 liter 3 necked flask equipped with a mechanical stirrer condenser, side arm with bubbler, thermometer and Claissen adapter was added 110 grams of hydroquinone, 1.0 grams of LiOH•H$_2$O and 230 grams of 98% propylene carbonate. The mixture was heated with stirring for 10 hours at 163°-168° C. 234 grams of product was obtained. GPC analysis in THF indicated a purity of 91.3% of 2,2'-[1,4-phenylene bis (oxy)] bis propanol.

Into a 1 liter 3 necked flask equipped with a mechanical stirrer, Claissen adaptor attached to a distillation head, thermometer, overhead takeoff, ice bath and vacuum means was charged 180 grams of the ester product of Example 3, 60.0 grams of the above reaction mixture containing the ether alkyl alcohol intermediate and 1.0 grams of LiOH•H$_2$O. The reaction mixture was heated with vacuum with stirring for 2 hours at 165°-167° C.

211 grams of product was obtained. GPC analysis indicated 53.0% of the disubstituted product and 31.0% of the monosubstituted product.

EXAMPLE 16

Preparation of 3-(n-dodecylthio)propanoic acid, 2,2'-[1,2-phenylene bis (oxy)] bis ethyl diester Into a 1 liter 3 necked flask equipped with a mechanical stirrer condenser, side arm with bubbler, thermometer and Claissen adapter was added 110 grams of 99% pyrocatechol, 1.0 grams of LiOH•H$_2$O and 193.6 grams of 98% ethylene carbonate. The mixture was heated with stirring for 5 ½ hours at 152°-154° C. 206 grams of product was obtained. GPC analysis in THF indicated a purity of 92.4% of 2,2'-[1,2-phenylene bis (oxy)] bis ethanol.

Into a 1 liter 3 necked flask equipped with a mechanical stirrer, Claissen adaptor attached to a distillation head, thermometer, overhead takeoff, ice bath and vacuum means was charged 145.5 grams of the ester product of Example 2, 51.5 grams of the above reaction mixture containing the ether alkyl alcohol intermediate and 0.5 grams of LiOH•H$_2$O. The reaction mixture was heated with vacuum with stirring for 2 ½ hours at 168°-174° C.

176.5 grams of product was obtained. GPC analysis indicated 89.6% of the disubstituted product.

EXAMPLE 17

Preparation of 3-(n-dodecylthio)propanoic acid, 2,2'-[1,2-phenylene bis (oxy)] bis propyl diester Into a 1 liter 3 necked flask equipped with a mechanical stirrer condenser, side arm with bubbler, thermometer and Claissen adapter was added 110 grams of 99% pyrocatechol, 1.0 grams of LiOH•H$_2$O and 230 grams of 98% propylene carbonate. The mixture was heated with stirring for 5 ½ hours at 178°-186° C. 237 grams of product was obtained. GPC analysis in THF indicated a purity of 95.5% of 2,2'-[1,2-phenylene bis (oxy)] bis propanol.

Into a 1 liter 3 necked flask equipped with a mechanical stirrer, Claissen adaptor attached to a distillation head, thermometer, overhead takeoff, ice bath and vacuum means was charged 145.5 grams of the ester product of Example 2, 59.25 grams of the above reaction mixture containing the ether alkyl alcohol intermediate and 0.5 grams of LiOH•H$_2$O. The reaction mixture was heated with vacuum with stirring for 2 hours at 152°-162° C.

188 grams of product was obtained. GPC analysis indicated 65.3% of the disubstituted product and 23.9% of the monosubstituted product.

EXAMPLE 18

Preparation of 3-(n-dodecylthio)propanoic acid, 2,2'-[1,2-phenylene bis (oxy)] ethyl propyl diester mixture Into a 1 liter 3 necked flask equipped with a mechanical stirrer condenser, side arm with bubbler, thermometer and Claissen adapter was added 88 grams of 99% pyrocatechol, 0.25 grams of KOH and 158 grams of Texacor TM EC-50 (50% ethylene carbonate and 50% propylene carbonate). The mixture was heated under a N$_2$ blanket with stirring for 6 ½ hours at 155°-182° C. 172 grams of product was obtained. GPC analysis in THF indicated a purity of 86.6% of 2,2'-[1,2-phenylene bis (oxy)] ethanol, propanol mixture.

Into a 1 liter 3 necked flask equipped with a mechanical stirrer, Claissen adaptor attached to a distillation head, thermometer, overhead takeoff, ice bath and vacuum means was charged 157.0 grams of the ester product of Example 1, 53.75 grams of the above reaction mixture containing the ether alkyl alcohol intermediate and 0.25 grams of KOH. The reaction mixture was heated with vacuum with stirring for 2 ½ hours at 145°-157° C.

194 grams of product was obtained.

EXAMPLE 19

Preparation of 3-(n-dodecylthio)propanoic acid, 2,2'-[1,3-phenylene bis (oxy)] bis ethyl diester Into a 1 liter 3 necked flask equipped with a mechanical stirrer condenser, side arm with bubbler, thermometer and Claissen adapter was added 110 grams of resorcinol, 1.0 grams of LiOH and 187 grams of 98% propylene carbonate. The mixture was heated with stirring for 4 hours at 165°-182° C. 203 grams of product was obtained. GPC analysis in THF indicated a purity of 98.1% of 2,2'-[1,3-phenylene bis (oxy)] bis ethanol.

Into a 1 liter 3 necked flask equipped with a mechanical stirrer, Claissen adaptor attached to a distillation head, thermometer, overhead takeoff, ice bath and vacuum means was charged 145.5 grams of the ester product of Example 2, 50.75 grams of the above reaction mixture containing the ether alkyl alcohol intermediate and 0.5 grams of LiOH•H$_2$O. The reaction mixture was heated with vacuum with stirring for 4 hours at 152°-159° C.

179.5 grams of product was obtained. GPC analysis indicated 71.6% of the disubstituted product and 19.8% of the monosubstituted product.

EXAMPLE 20

Preparation of 3-(n-dodecylthio)propanoic acid, 2-(2,4-dimethyl phenoxy) ethyl ester Into a 1 liter 3 necked flask equipped with a mechanical stirrer condenser, side arm with bubbler, thermometer and Claissen adapter was added 122 grams of 97% 2,4-dimethylphenol, 1.0 grams of LiOH•H$_2$O and 98 grams of 98% ethylene carbonate. The mixture was heated with stirring for 6 ½ hours at 156°-158° C. 173 grams of product was obtained. GPC analysis in THF indicated a purity of 95.1% of 2-(2,4-dimethylphenoxy) ethanol.

Into a 1 liter 3 necked flask equipped with a mechanical stirrer, Claissen adaptor attached to a distillation head, thermometer, overhead takeoff, ice bath and vacuum means was charged 145.5 grams of the ester product of Example 2, 86.5 grams of the above reaction mixture containing the ether alkyl alcohol intermediate and 0.5 grams of LiOH•H$_2$O. The reaction mixture was heated with vacuum with stirring for 1 hour at 155°-157° C.

212 grams of product was obtained. GPC analysis indicated 85.9% of the desired product.

EXAMPLE 21

Preparation of 3-(n-dodecylthio)propanoic acid, 2-(4-isopropyl phenoxy) ethyl ester Into a 1 liter 3 necked flask equipped with a mechanical stirrer condenser, side arm with bubbler, thermometer and Claissen adapter was added 136 grams of 99% p-isopropylphenol, 1.0 grams of LiOH•H$_2$O and 96 grams of 98% ethylene carbonate. The mixture was heated with stirring for 7 hours at 156°-159° C. 185 grams of product was obtained. GPC analysis in THF indicated a purity of 97.1% of 2-(4-isopropylphenoxy) ethanol.

Into a 1 liter 3 necked flask equipped with a mechanical stirrer, Claissen adaptor attached to a distillation head, thermometer, overhead takeoff, ice bath and vacuum means was charged 145.5 grams of the ester product of Example 2, 92.5 grams of the above reaction mixture containing the ether alkyl alcohol 25 intermediate and 0.5 grams of LiOH•H$_2$O. The reaction mixture was heated with vacuum with stirring for 2 hours at 157°-160° C.

219 grams of product was obtained. GPC analysis indicated 84.6% of the desired product.

EXAMPLE 22

Preparation of 3-(n-dodecylthio)propanoic acid, 2-(4-sec-butyl phenoxy) propyl ester Into a 1 liter 3 necked flask equipped with a mechanical stirrer condenser, side arm with bubbler, thermometer and Claissen adapter was added 150.2 grams of 98% secondary butyl phenol, 2.0 grams of LiOH•H$_2$O and 107.2 grams of propylene carbonate. The mixture was heated with stirring for 6 hours at 185°-187° C. 212.5 grams of product was obtained. GPC analysis in THF indicated a purity of 97.0% of 2-(4-sec-butylphenoxy) propanol.

Into a 1 liter 3 necked flask equipped with a mechanical stirrer, Claissen adaptor attached to a distillation head, thermometer, overhead takeoff, ice bath and vacuum means was charged 155.5 grams of the ester product of Example 1, 106.25 grams of the above reaction mixture containing the ether alkyl alcohol intermediate and 1.0 grams of LiOH•H$_2$O. The reaction mixture was heated with vacuum with stirring for 1.5 hours at 145°-155° C.

243 grams of product was obtained.

EXAMPLE 23

Preparation of 3-(n-dodecylthio)propanoic acid, 2-(4-nonyl phenoxy) ethyl ester

Into a 1 liter 3 necked flask equipped with a mechanical stirrer condenser, side arm with bubbler, thermometer and Claissen adapter was added 220 grams of 95% p-mononylphenol, 2.0 grams of LiOH•H$_2$O and 92.4 grams of 98% ethylene carbonate. The mixture was heated with stirring for 6 hours at 180°-186° C. 270.5 grams of product was obtained. GPC analysis in THF indicated a purity of 97.1% of 2-(4-nonylphenoxy) ethanol.

Into a 1 liter 3 necked flask equipped with a mechanical stirrer, Claissen adaptor attached to a distillation head, thermometer, overhead takeoff, ice bath and vacuum means was charged 76.65 grams of the ester product of Example 1, 67.63 grams of the above reaction mixture containing the ether alkyl alcohol intermediate and 0.25 grams of LiOH•H$_2$O. The reaction mixture was heated with vacuum with stirring for 1.5 hours at 145°-150° C.

136 grams of product was obtained. GPC analysis indicated 88.99% of the desired product.

EXAMPLE 24

Preparation of 3-(n-dodecylthio)propanoic acid, 2-(4-nonyl phenoxy) propyl ester Into a 1 liter 3 necked flask equipped with a mechanical stirrer condenser, side arm with bubbler, thermometer and Claissen adapter was added 220 grams of 95% p-mononylphenol, 2.0 grams of LiOH•H$_2$O and 107.2 grams of propylene carbonate. The mixture was heated with stirring for 6 hours at 188°-192° C. 278 grams of product was obtained. GPC analysis in THF indicated a purity of 94.7% of 2-(4-nonylphenoxy) propanol.

Into a 1 liter 3 necked flask equipped with a mechanical stirrer, Claissen adaptor attached to a distillation head, thermometer, overhead takeoff, ice bath and vacuum means was charged 145 grams of the ester product of Example 1, 139.5 grams of the above reaction mixture containing the ether alkyl alcohol intermediate and 0.5 grams of LiOH•H$_2$O. The reaction mixture was heated with vacuum with stirring for 1 hour at 172°-174° C.

266 grams of product was obtained. GPC analysis indicated 78.5% of the desired product.

EXAMPLE 25

Preparation of 3-(n-dodecylthio)propanoic acid, 2-(2,4-dinonyl phenoxy) ethyl ester Into a 1 liter 3 necked flask equipped with a mechanical stirrer condenser, side arm with bubbler, thermometer and Claissen adapter was added 346 grams of dinonylphenol, 2.0 grams of LiOH•H$_2$O and 92.4 grams of 98% propylene carbonate. The mixture was heated with stirring for 4 hours at 158°-167° C. and 1 hour at 185°-192° C. 392 grams of product was obtained. GPC analysis in THF indicated a purity of 93.2% of 2-(2,4-dinonylphenoxy) ethanol.

Into a 1 liter 3 necked flask equipped with a mechanical stirrer, Claissen adaptor attached to a distillation head, thermometer, overhead takeoff, ice bath and vacuum means was charged 120 grams of the ester product of Example 1, 153 grams of the above reaction mixture containing the ether alkyl alcohol intermediate and 0.75 grams of LiOH•H$_2$O. The reaction mixture was heated with vacuum with stirring for 1.5 hours.

260.75 grams of product was obtained. GPC analysis indicated 79.5% of the desired product.

EXAMPLE 26

Preparation of 3-(n-dodecylthio)propanoic acid, 2-(2,4-dinonyl phenoxy) propyl ester Into a 1 liter 3 necked flask equipped with a mechanical stirrer condenser, side arm with bubbler, thermometer and Caisson adapter was added 173 grams of dinonylphenol, 1.0 grams of LiOH•H$_2$O and 56 grams of propylene carbonate. The mixture was heated with stirring for 5 hours at 170°–175° C., 3 ½ hours at 172°–174° C. and 17 hours at 172°–177° C. 202 grams of product was obtained. GPC analysis in THF indicated a purity of 93.6% of 2-(2,4-dinonylphenoxy) propanol.

Into a 1 liter 3 necked flask equipped with a mechanical stirrer, Claissen adaptor attached to a distillation head, thermometer, overhead takeoff, ice bath and vacuum means was charged 72.75 grams of the ester product of Example 2, 101.0 grams of the above reaction mixture containing the ether alkyl alcohol intermediate and 0.5 grams of LiOH•H$_2$O. The reaction mixture was heated with vacuum with stirring for 1 hour at 172°–174° C.

162 grams of product was obtained. GPC analysis indicated 26.3% of the desired product.

EXAMPLE 27

Preparation of 3-(n-dodecylthio)propanoic acid, 2-(4-isopropyl phenoxy) propyl ester Into a 1 liter 3 necked flask equipped with a mechanical stirrer condenser, side arm with bubbler, thermometer and Claissen adapter was added 136 grams of 99% p-isopropylphenol, 1.5 grams of LiOH•H$_2$O and 107.2 grams of propylene carbonate. The mixture was heated with stirring for 6 hours at 178°–182° C. 199 grams of product was obtained. GPC analysis in THF indicated a purity of 83.8% of 2-(4-isopropylphenoxy) propanol.

Into a 1 liter 3 necked flask equipped with a mechanical stirrer, Claissen adaptor attached to a distillation head, thermometer, overhead takeoff, ice bath and vacuum means was charged 160 grams of the ester product of Example 1, 100.0 grams of the above reaction mixture containing the ether alkyl alcohol intermediate and 1.0 grams of LiOH•H$_2$O. The reaction mixture was heated with vacuum with stirring for 1.5 hours at 165°–178° C.

237 grams of product was obtained.

EXAMPLE 28

Preparation of 3-(n-dodecylthio)propanoic acid, 2,2'-[4,4'-(dimethylmethylene bis) phenoxy] bis ethyl diester Into a 1 liter 3 necked flask equipped with a mechanical stirrer condenser, side arm with bubbler, thermometer and Claissen adapter was added 114 grams of Bisphenol A, 1.0 grams of LiOH•H$_2$O and 96 grams of 98% ethylene carbonate. The mixture was heated with stirring for 5 hours at 153°–156° C. 157 grams of product was obtained. GPC analysis in THF indicated a purity of 96.6% of 2,2'-[4,4'-dimethylmethylene bis) phenoxy] bis ethanol.

Into a 1 liter 3 necked flask equipped with a mechanical stirrer, Claissen adaptor attached to a distillation head, thermometer, overhead takeoff, ice bath and vacuum means was charged 153.5 grams of the ester product of Example 1, 83.5 grams of the above reaction mixture containing the ether alkyl alcohol intermediate and 0.5 grams of LiOH•H$_2$O. The reaction mixture was heated with vacuum with stirring for 1 hour at 145°–153° C.

219 grams of product was obtained. GPC analysis indicated 80.0% of the disubstituted product and 12.2% of the monosubstituted product.

EXAMPLE 29

Preparation of 3-(n-dodecylthio)propanoic acid, 2,2'-[4,4'-dimethylmethylene bis) phenoxy] bis propyl diester Into a 1 liter 3 necked flask equipped with a mechanical stirrer condenser, side arm with bubbler, thermometer and Claissen adapter was added 114 grams of Bisphenol A, 1.0 grams of LiOH•H$_2$O and 110 grams of propylene carbonate. The mixture was heated with stirring for 6 hours at 175°–180° C. 177 grams of product was obtained. GPC analysis in THF indicated a purity of 95.0% of 2,2'-[4,4'-(dimethylmethylene bis) phenoxy] bis propanol.

Into a 1 liter 3 necked flask equipped with a mechanical stirrer, Claissen adaptor attached to a distillation head, thermometer, overhead takeoff, ice bath and vacuum means was charged 153.5 grams of the ester product of Example 1, 88.5 grams of the above reaction mixture containing the ether alkyl alcohol intermediate and 1.0 grams of LiOH•H$_2$O. The reaction mixture was heated with vacuum with stirring for 1 hour at 153°–156° C.

222.5 grams of product was obtained. GPC analysis indicated 62.5% of the disubstituted product and 28.2% of the monosubstituted product.

EXAMPLE 30

Preparation of 3-(n-dodecylthio)propanoic acid, 2,2'-4,4'-(dimethylmethylene bis) phenoxy] ethyl propyl diester mixture Into a 1 liter 3 necked flask equipped with a mechanical stirrer, side arm with bubbler, thermometer and Claissen adapter was added 228 grams of Bisphenol A, 0.1 grams of KOH and 90 grams of 98% ethylene carbonate. The mixture was heated with stirring for 2 hours at 185°–188° C. and for 4 hours at 200°–205° C. 326 grams of product was obtained.

Into a 1 liter 3 necked flask equipped with a mechanical stirrer, Claissen adaptor attached to a distillation head, thermometer, overhead takeoff, ice bath and vacuum means was charged 157 grams of the ester product of Example 1, 82.5 grams of the above reaction mixture containing the ether alkyl alcohol intermediate and 0.5 grams of KOH. The reaction mixture was heated with vacuum with stirring for 2 hours at 165°–170° C.

222 grams of product was obtained.

EXAMPLE 31

Preparation of 3-(n-dodecylthio)propanoic acid, 2,2'-[1,1'-biphenyl-4,4'-bis (oxy)] bis propyl diester Into a 1 liter 3 necked flask equipped with a mechanical stirrer condenser, side arm with bubbler, thermometer and Claissen adapter was added 186 grams of 4,4-dihydroxydiphenyl, 0.5 grams of KOH and 214 grams of propylene carbonate. The mixture was heated with stirring for 1 hour at 145°–155° C. and 2 hours at 155°–168° C., 1 hour at 168°–180° C. and 2 hours at 180°–208° C. 304 grams of product was obtained.

Into a 1 liter 3 necked flask equipped with a mechanical stirrer, Claissen adaptor attached to a distillation head, thermometer, overhead takeoff, ice bath and vacuum means was charged 157.0 grams of the ester product of Example 1, 76.0 grams of the above reaction mixture containing the ether alkyl alcohol intermediate and 0.2 grams of KOH. The reaction mixture was heated with vacuum with stirring for 2 hours at 185°–188° C.

218 grams of product was obtained.

EXAMPLE 32

Preparation of 3-(n-dodecylthio)propanoic acid, 2,2'-[naphthylene-1,5-bis (oxy)] bis propyl diester Into a 1 liter 3 necked flask equipped with a mechanical stirrer condenser, side arm with bubbler, thermometer and Claissen adapter was added 80 grams of 97% 1,5-naphthalenediol, 0.25 grams of KOH and 107 grams of propylene carbonate. The mixture was heated with stirring under a $N_2$ atmosphere for 1 hour at 165°–190° C. and 5 hours at 190°–206° C. 139 grams of product was obtained. GPC analysis in THF indicated a purity of 97.8% of 2,2'-[naphthylene-1,5-bis (oxy)] bis propanol.

Into a 1 liter 3 necked flask equipped with a mechanical stirrer, Claissen adaptor attached to a distillation head, thermometer, overhead takeoff, ice bath and vacuum means was charged 157 grams of the ester product of Example 1, 69.5 grams of the above reaction mixture containing the ether alkyl alcohol intermediate and 0.5 grams of LiOH•$H_2O$. The reaction mixture was heated with vacuum with stirring for 2 hours at 161°–165° C.

210 grams of product was obtained. GPC analysis indicated a purity of 65.7% of desired product.

EXAMPLE 33

Preparation of 3-(n-dodecylthio)propanoic acid, 2,2'-[naphthylene-1,5-bis (oxy)] ethyl, propyl diester mixture Into a 1 liter 3 necked flask equipped with a mechanical stirrer condenser, side arm with bubbler, thermometer and Claissen adapter was added 80 grams of 97% 1,5-napthalenediol, 0.25 grams of KOH and 99 grams of 5C-50(50% ethylene carbonate and 50% propylene carbonate). The mixture was heated with stirring under a $N_2$ atmosphere for 1 hour at 145°–183° C. and for 5 hours at 183°–185° C. 133 grams of product was obtained. GPC analysis in THF indicated a purity of 98.1% of 2,2'-[1,2-phenylene bis (oxy)] bis propanol.

Into a 1 liter 3 necked flask equipped with a mechanical stirrer, Claissen adaptor attached to a distillation head, thermometer, overhead takeoff, ice bath and vacuum means was charged 157.0 grams of the ester product of Example 1, 66.5 grams of the above reaction mixture containing the ether alkyl alcohol intermediate and 0.5 grams of KOH. The reaction mixture was heated with vacuum with stirring for 1 hour at 145°–155° C. and 2 hours at 155°–170° C.

206 grams of product was obtained.

EXAMPLE 34

Preparation of 3-(n-dodecylthio)propanoic acid, 2,2'-[2,5-di-tert-butyl-1,4-phenylene bis (oxy)] bis ethyl diester Into a 1 liter 3 necked flask equipped with a mechanical stirrer condenser, side arm with bubbler, thermometer and Claissen adapter was added 170 grams of 97% 2,5-tertiarybutyl hydroquinone, 0.75 grams of KOH and 139.4 grams of 98% ethylene carbonate. The mixture was heated with stirring for 14 hours at 145°–150° C. 241 grams of product was obtained.

Into a 1 liter 3 necked flask equipped with a mechanical stirrer, Claissen adaptor attached to a distillation head, thermometer, overhead takeoff, ice bath and vacuum means was charged 157 grams of the ester product of Example 1, 79.0 grams of the above reaction mixture containing the ether alkyl alcohol intermediate and 0.5 grams of KOH. The reaction mixture was heated with vacuum with stirring for 2 hours at 165°–173° C.

218.8 grams of product was obtained.

EXAMPLE 35

Preparation of 3-(n-dodecylthio)propanoic acid, 2,2'-[2,5-di-tert-butyl-1,4-phenylene bis (oxy)] bis propyl diester Into a 1 liter 3 necked flask equipped with a mechanical stirrer condenser, side arm with bubbler, thermometer and Claissen adapter was added 222 grams of 97% 2,5-ditert.butyl hydroquinone, 1.0 grams of KOH and 214 grams of propylene carbonate. The mixture was heated with stirring for 8 hours at 140°–155° C. 343 grams of product was obtained.

Into a 1 liter 3 necked flask equipped with a mechanical stirrer, Claissen adaptor attached to a distillation head, thermometer, overhead takeoff, ice bath and vacuum means was charged 157 grams of the ester product of Example 1, 85.75 grams of the above reaction mixture containing the ether alkyl alcohol intermediate and 0.25 grams of KOH. The reaction mixture was heated with vacuum with stirring for 3 hours at 175°–182° C.

228 grams of product was obtained.

EXAMPLE 36

Preparation of 3-(crude secondary dodecylthio) propanoic acid, methyl ester

Into a 1 liter 3 necked flask equipped with a mechanical stirrer condenser, side arm with bubbler, thermometer and Claissen adapter was added 110 grams of hydroquinone, 2.8 grams of tetraethylammonium bromide and 202 grams of 98% ethylene carbonate. The mixture was heated with stirring for 6 hours at 148°–154° C. 209 grams of product was obtained. GPC analysis in THF indicated a purity of 92.4% of 2,2'-[1,4-phenylene bis (oxy)] bis ethanol.

Into a 1 liter 3 necked flask equipped with a mechanical stirrer, Claissen adaptor attached to a distillation head, thermometer, overhead takeoff, ice bath and vacuum means was charged 150 grams of the ester product of Example 7, 52 grams of the above reaction mixture containing the ether alkyl alcohol intermediate and 1.5 grams of dibutyltin oxide. The reaction mixture was heated with vacuum with stirring for 2 hours at 148°–154° C.

188 grams of product was obtained. GPC analysis indicated 31.4% of the disubstituted product and 34.1% of the monosubstituted product.

EXAMPLE 37

A 1.0 percent by weight toluene solution of various thioesters of the present invention was added to a SBR-toluene solution. Ester A was 3-(n-dodecylthio)-propanoic acid, 2,2'-[1,4- phenylene bis (oxy)] bis ethyl diester prepared in accordance with Example 9. Ester B was 3-(crude secondary dodecylthio)propanoic acid, methyl ester and prepared in accordance with Example 36. Ester C was 3-(n-dodecylthio)-propanoic acid, 2,2'-

[1,4-phenylene bis (oxy)] bis propyl diester and prepared in accordance with Example 12. Various phenolic antioxidants were sometimes used. Wingstay ®-C is an alkylated hindered phenol which is commercially available from The Goodyear Tire & Rubber Company. Wingstay ®-S is a styrenated phenol which is commercially available from The Goodyear Tire & Rubber Company. Wingstay ®-L is a butylated reaction product of p-cresol and dicyclopentadiene. BHT is 2,6-ditertiary-butyl p-cresol. Antioxidant 451 (A0451) is an alkylated hydroquinone which is commercially available from Uniroyal. DNP is dinonylphenol. Table I below lists the antioxidant, synergist and hours to 1 percent O₂ uptake in an oxygen absorption test. Table II illustrates the use of the esters of the present invention (Esters A-C) in combination with conventional phenolic antioxidants versus use of Wingstay ® SN-1, 3,6,9-trioxaundecane-1,11-bis-(3-n-dodecylthio-propionate) in combination with the same conventional phenolic antioxidants.

TABLE I

| Sample | Antioxidant (Parts) | Synergist Parts | Hours to 1% O₂ Uptake @ 100° C. |
|---|---|---|---|
| 1 | .5 Wingstay ®-C | 0 | 202 |
| 2 | .5 Wingstay ®-S | 0 | 118 |
| 3 | .5 Wingstay ®-L | 0 | 361 |
| 4 | .5 BHT | 0 | 368 |
| 5 | .5 DNP | 0 | 93 |
| 6 | | .5 Ester A | 84 |
| 7 | | .5 Ester B | 81 |
| 8 | | .5 Ester C | 72 |
| 9 | .5 Wingstay ®-C | .5 Ester D | 945 |
| 10 | .5 Wingstay ®-S | .5 Ester D | 943 |
| 11 | .5 Wingstay ®-L | .5 Ester D | 1270 |
| 12 | .5 BHT | .5 Ester D | 822 |
| 13 | .5 DNP | .5 Ester D | 1055 |
| 14 | .5 Wingstay ®-C | .5 Ester A | 1123 |
| 15 | .5 Wingstay ®-S | .5 Ester A | 1659 |
| 16 | .5 Wingstay ®-L | .5 Ester A | 1796 |
| 17 | .5 BHT | .5 Ester A | 1106 |
| 18 | .5 DNP | .5 Ester A | 1662 |
| 19 | .5 Wingstay ®-C | .5 Ester B | 1112 |
| 20 | .5 Wingstay ®-S | .5 Ester B | 1386 |
| 21 | .5 Wingstay ®-L | .5 Ester B | 1686 |
| 22 | .5 BHT | .5 Ester B | 1048 |
| 23 | .5 DNP | .5 Ester B | 1440 |
| 24 | .5 Wingstay ®-C | .5 Ester C | 1282 |
| 25 | .5 Wingstay ®-C | .5 Ester C | 1804 |
| 26 | .5 Wingstay ®-L | .5 Ester C | 2534 |
| 27 | .5 BHT | .5 Ester C | 1127 |
| 28 | .5 DNP | .5 Ester C | 1100 |

TABLE II

| Sample | Antioxidant (Parts) | Synergist (Parts) | Hours to 1% O₂ Uptake @ 100° C. | Improvement Over Control |
|---|---|---|---|---|
| 9 (Control) | .5 Wingstay ®-C | .5 SN-1 | 945 | — |
| 14 | .5 Wingstay ®-C | .5 Ester A | 1123 | 19% |
| 19 | .5 Wingstay ®-C | .5 Ester B | 1112 | 18% |
| 24 | .5 Wingstay ®-C | .5 Ester C | 1282 | 36% |
| 10 (Control) | .5 Wingstay ®-S | .5 SN-1 | 943 | — |
| 15 | .5 Wingstay ®-S | .5 Ester A | 1659 | 76% |
| 20 | .5 Wingstay ®-S | .5 Ester B | 1386 | 47% |
| 25 | .5 Wingstay ®-S | .5 Ester C | 1804 | 91% |
| 11 (Control) | .5 Wingstay ®-L | .5 SN-1 | 1270 | — |
| 16 | .5 Wingstay ®-L | .5 Ester A | 1796 | 41% |
| 21 | .5 Wingstay ®-L | .5 Ester B | 1686 | 33% |
| 26 | .5 Wingstay ®-L | .5 Ester C | 2534 | 100% |
| 12 (Control) | .5 BHT | .5 SN-1 | 822 | — |
| 17 | .5 BHT | .5 Ester A | 1106 | 35% |
| 22 | .5 BHT | .5 Ester B | 1048 | 27% |
| 27 | .5 BHT | .5 Ester C | 1127 | 37% |
| 13 (Control) | .5 DNP | .5 SN-1 | 1055 | — |
| 18 | .5 DNP | .5 Ester A | 1662 | 58% |
| 23 | .5 DNP | .5 Ester B | 1440 | 36% |
| 28 | .5 DNP | .5 Ester C | 1100 | 4% |

As can be seen from the above tables, the esters of the present invention yielded longer oxygen absorption values than use of Wingstay ® SN-1 3,6,9-trioxaundecane-1,11-bis(3-n-dodecylthiopropionate) when used with the various phenolic antioxidants.

What is claimed is:

1. A compound of the following structural formula:

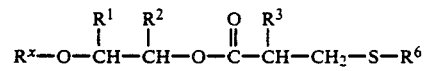

wherein $R^x$ is selected from the group of formulae consisting of:

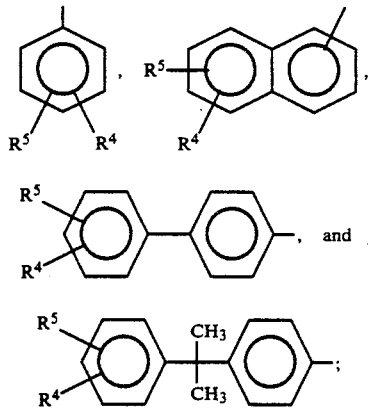

$R^1$, $R^2$ and $R^3$ are independently selected from the group consisting of hydrogen or methyl; $R^4$ and $R^5$ are independently selected from the group consisting of hydrogen, alkyl having 1 to 18 carbon atoms, aryls having 6 to 10 carbon atoms, aralkyls having 7 to 9 carbon atoms, and a radical of the formula:

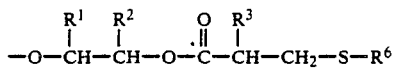

and R⁶ is selected from the group consisting of alkyls having 1 to 24 carbon atoms, aryls having 6 to 12 carbon atoms and aralkyls having 7 to 12 carbon atoms.

2. The compound of claim 1 wherein $R^x$ is:

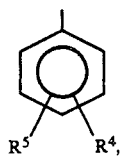

$R^1$ is methyl, $R^2$ is hydrogen, $R^3$ is hydrogen, $R^4$ is of the formula:

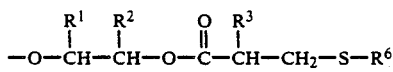

$R^5$ is hydrogen and $R^6$ is an alkyl having 6 to 14 carbon atoms.

3. An antioxidant system comprising (A) a thioester having the following structural formula:

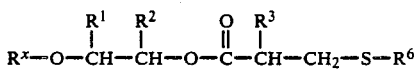

wherein $R^x$ is selected from the group of formulae consisting of:

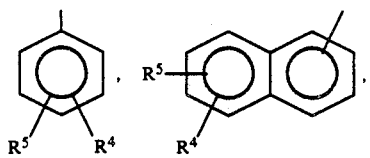

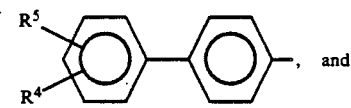

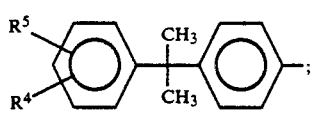

$R^1$, $R^2$ and $R^3$ are independently selected from the group consisting of hydrogen or methyl; $R^4$ and $R^5$ are independently selected from the group consisting of hydrogen, alkyls having 1 to 18 carbon atoms, aryls having 6 to 10 carbon atoms, aralkyls having 7 to 9 carbon atoms, and a radical of the formula:

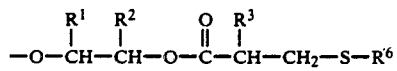

and R⁶ is selected from the group consisting of alkyls having 1 to 24 carbon atoms, aryls having 6 to 12 carbon atoms and aralkyls having 7 to 12 carbon atoms; and (B) an amine or phenolic antioxidant.

4. The antioxidant system of claim 3 wherein the weight ratio of the thioester to the amine or phenolic antioxidant ranges from about 10:1 to about 1:10.

5. The antioxidant system of claim 3 wherein the amine antioxidant is selected from the group consisting of polymerized and non-polymerized derivative of:

(A) 2,2,4trimethyl-1,2-dihydroquinoline;

(B) N,N'-di-substituted-p-phenylenediamines having the structural formula:

wherein $R^7$ and $R^8$ are independently selected from the group consisting of alkyls having 3 to 12 carbon atoms, aryls having 6 to 12 carbon atoms, and aralkyls having 7 to 12 carbon atoms;

(C) diphenylamines having the structural formula:

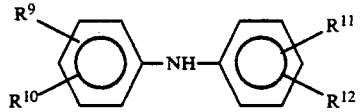

wherein $R^9$, $R^{10}$, $R^{11}$ and $R^{12}$ are independently selected from the group of radicals consisting of hydrogen, alkyls having 1 to 20 carbon atoms and aralkyls having 7 to 12 carbon atoms;

(D) amides having the structural formula:

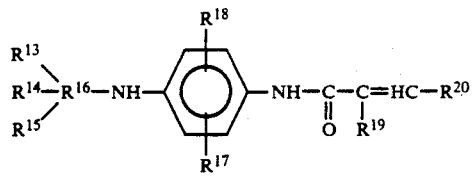

wherein $R^{16}$ is selected from the group of radicals consisting of arylenes having 6 to 12 carbon atoms, $R^{13}$ and $R^{14}$ are independently selected from the group of radicals consisting of hydrogen, alkyls having from 1 to 4 carbon atoms and alkoxys having from 1 to 4 carbon atoms, $R^{15}$ is selected from the group of radicals consisting of hydrogen, alkyls having from 1 to 4 carbon atoms, alkoxys having from 1 to 4 carbon atoms and a radical having the following structural formula:

wherein $R^{21}$ is selected from the group of radicals consisting of alkyls having from 1 to 12 carbon atoms, aryls having from 6 to 12 carbon atoms and aralkyls having from 7 to 13 carbon atoms and $R^{22}$ is selected from the group of radicals consisting of hydrogen and alkyls having from 1 to 12 carbon atoms and wherein $R^{17}$ and $R^{18}$ are selected from the group of radicals consisting of hydrogen, alkyls having from 1 to 4 carbon atoms, $R^{19}$ is selected from the group of radicals consisting of hydrogen, alkyls having from 1 to 4 carbon atoms, aryls having from 6 to 12 carbon atoms, aralkyls having from 7 to 13 carbon atoms, cycloalkyls having from 5 to 12 carbon atoms, carboxymethyl radicals and carbalkoxymethyl radicals, and $R^{20}$ is selected from the group of radicals consisting of hydrogen, alkyls having from 1 to 4 carbon atoms, aryls having from 6 to 12 carbon atoms, cycloalkyls having from 5 to 12 carbon atoms, carboxyl radicals and carbalkoxy radicals, and;

(E) imides having the structural formula:

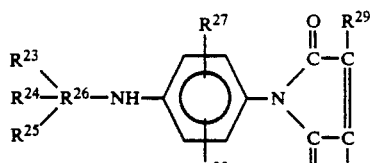

and

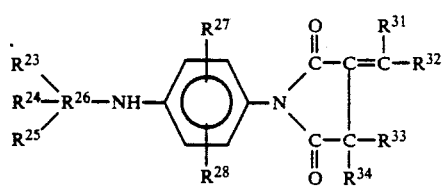

wherein $R^{26}$ is selected from the group of radicals consisting of arylenes having 6 to 12 carbon atoms, $R^{23}$ and $R^{24}$ are independently selected from the group of radicals consisting of hydrogen, alkyls having from 1 to 4 carbon atoms and alkoxys having from 1 to 4 carbon atoms, $R^{25}$ is selected from the group of radicals consisting of hydrogen, alkyls having from 1 to 4 carbon atoms, alkoxys having from 1 to 4 carbon atoms and a radical having the following structural formula:

wherein $R^{35}$ is selected from the group of radicals consisting of alkyls having from 1 to 12 carbon atoms, cycloalkyls having from 5 to 12 carbon atoms, aryls having from 6 to 12 carbon atoms and aralkyls having from 7 to 13 carbon atoms and $R^{36}$ is selected from the group of radicals consisting of hydrogen and alkyls having from 1 to 12 carbon atoms and wherein $R^{27}$ and $R^{28}$ are alkyls having from 1 to 4 carbon atoms, and wherein $R^{29}$, $R^{30}$, $R^{31}$, $R^{32}$, $R^{33}$ and $R^{34}$ are independently selected from the group of radicals consisting of hydrogen and alkyls having 1 to 4 carbon atoms.

6. The antioxidant system of claim 3 wherein the phenolic antioxidant is selected from the group consisting of:

(A) trialkylated phenolic antioxidants having the structural formula:

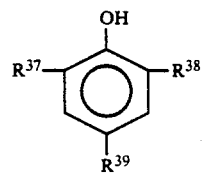

wherein $R^{37}$ and $R^{38}$ are selected from the group consisting of hydrogen, tertiary alkyls having 4 to 9 carbon atoms, cycloalkyls having 5 to 12 carbon atoms and aralkyls having 7 to 12 carbon atoms and wherein $R^{39}$ is selected from the group consisting of alkyls having 1 to 20 carbon atoms, cycloalkyls having 5 to 12 carbon atoms and aralkyls having 7 to 12 carbon atoms;

(B) alkylated reaction products of phenols and dicyclopentadiene;

(C) styrenated phenols; and (D) alkylated hydroquinone.

7. The antioxidant system of claim 4 wherein the weight ratio of the thioester to the amine or phenolic antioxidant ranges from about 5:1 to 1:5.

8. The antioxidant system of claim 3 wherein $R^x$ is:

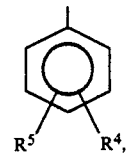

$R^1$ is methyl, $R^2$ is hydrogen, $R^3$ is hydrogen, $R^4$ is a radical of the formula:

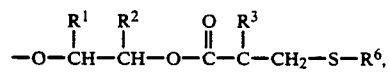

$R^5$ is hydrogen and $R^6$ is an alkyl having 6 to 14 carbon atoms.

* * * * *